United States Patent [19]

Bremer

[11] Patent Number: 4,753,223
[45] Date of Patent: Jun. 28, 1988

[54] SYSTEM FOR CONTROLLING SHAPE AND DIRECTION OF A CATHETER, CANNULA, ELECTRODE, ENDOSCOPE OR SIMILAR ARTICLE

[76] Inventor: Paul W. Bremer, c/o 433 Margaret St., Jacksonville, Fla. 32204

[21] Appl. No.: 927,861

[22] Filed: Nov. 7, 1986

[51] Int. Cl.[4] .............................................. A61B 1/00
[52] U.S. Cl. .......................................... 128/4; 604/95
[58] Field of Search .................................... 128/4–8, 128/419 P, 786; 604/53, 95; 60/527

[56] References Cited

U.S. PATENT DOCUMENTS

| | | |
|---|---|---|
| 3,043,309 | 1/1962 | McCarthy . |
| 3,162,214 | 12/1964 | Bazinet ..................... 128/4 |
| 3,605,725 | 9/1971 | Bentov . |
| 3,674,014 | 7/1972 | Tillander . |
| 3,773,034 | 11/1973 | Burns et al. . |
| 3,890,977 | 6/1975 | Wilson . |
| 3,938,502 | 2/1976 | Bom ....................... 128/660 |
| 4,037,411 | 7/1977 | Hochstein ................. 60/527 |
| 4,142,531 | 3/1979 | Magovern et al. ........... 128/419 P |
| 4,146,019 | 3/1979 | Bass et al. . |
| 4,176,662 | 12/1979 | Frazer . |
| 4,327,711 | 5/1982 | Takagi ...................... 128/4 |
| 4,329,980 | 5/1982 | Terada ...................... 128/4 |
| 4,411,655 | 10/1983 | Schreck . |
| 4,503,676 | 3/1985 | Rutledge . |
| 4,503,842 | 3/1985 | Takayama ................... 128/4 |
| 4,543,090 | 11/1985 | McCoy . |
| 4,556,050 | 12/1985 | Hodgson et al. . |
| 4,559,951 | 12/1985 | Dahl et al. . |
| 4,601,283 | 7/1986 | Chikama ..................... 128/4 |
| 4,643,202 | 2/1987 | Roche ..................... 128/786 |

Primary Examiner—Max Hindenburg
Attorney, Agent, or Firm—Nixon & Vanderhye

[57] ABSTRACT

A steerable medical probe device, such as a catheter, comprises a flexible, inner tubular body, a plurality of electrical conductors wrapped about the inner tubular body; and an insulating layer surrounding the conductors. Rigid non-conductive rings are adhesively secured at axially spaced locations along the distal end of the probe. A plurality of shape memory titanium-nickel wires extend between adjacent pairs of rings, and are electrically connected to a control device and power source. The control device may be operated to apply low current pulses selectively through one or more of the wires to effect contraction of the heated wires and thereby cause the distal end of the probe to bend in a desired direction.

18 Claims, 2 Drawing Sheets

SYSTEM FOR CONTROLLING SHAPE AND DIRECTION OF A CATHETER, CANNULA, ELECTRODE, ENDOSCOPE OR SIMILAR ARTICLE

BACKGROUND

This invention relates to catheters, cannulae, endoscopes and similar flexible probe devices. These devices are typically passed into and through a body orifice, incision, artery, vein or other passage until they have reached a desired position within the body. Probe devices of this kind often include fiber optic bundles for illumination and/or viewing purposes, and, depending on the particular device, feed lines for air or other fluid, and channels for suction, forceps, and the like. See, for example, U.S. Pat. No. 4,559,951.

Of great concern with such devices is their flexibility and steerability, characteristics which significantly bear on the ease with which the device can be introduced and passed through the various channels of the human, or animal body.

Various attempts have been made to produce a catheter, cannulae, endoscope or the like which is readily insertable and manipulatable for ease of advancement through body cavities or channels. See, for example, U.S. Pat. No. 4,543,090 which discloses a catheter having a distal end for ready insertion into a body, with a plurality of temperature-activated memory elements in its distal end. Each memory element assumes a first shape in response to temperature and a second shape in response to a force. The memory elements are coupled together and to a control means for deflecting the distal end of the catheter in a plurality of directions to steer or aim it within the body.

In U.S. Pat. No. 4,176,662 an endoscope is disclosed which includes a propulsion system consisting of two radially expandable bladders separated by an axially expandable bellows. In this device, only the forward bladder is attached to the distal end of the endoscope so that by expanding and contracting the bladders in proper sequence, propulsion of the endoscope is achieved.

U.S. Pat. No. 3,890,977 discloses a biological catheter or cannulae which incorporates material such as a titanium-nickel alloy having a heat activated shape memory. The device is formed and annealed at high temperature into a shape for effective anchoring or proper location in an organ or other structure of the body. At a temperature below its transitional temperature, it is reformed into a shape for ease of insertion, and when located as desired, it is heated above its transitional temperature to assume its proper anchoring or locating shape.

The catheter disclosed in U.S. Pat. No. 3,773,034 bends the distal end of a catheter as desired, utilizing a fluid.

The catheter disclosed in U.S. Pat. No. 3,674,014 includes permanent magnets and a magnetic field to bend the distal end of a catheter.

U.S. Pat. No. 3,605,725 utilizes mechanically manipulatable control reins to steer a catheter, while U.S. Pat. No. 3,043,309 discloses electromagnetic means for directing a tube in an intestinal intubation procedure.

Other prior art patents relevant to the use of heat activated shape memory alloy metals in medical devices include U.S. Pat. Nos. 4,556,050 and 4,411,655.

The principal object of this invention is to utilize shape memory metal technology to provide a steerable catheter, cannulae, electrode, endoscope and the like for easy insertion and advancement within the body.

To this end, the invention in its broader aspects, and in accordance with one exemplary embodiment, includes an elongated, flexible tubular body of multi-layered wall construction having proximal and distal ends; a plurality of sets of electrical conductors integrally contained within the multi-layered wall construction; at least one pair of relatively rigid rings encircling and fixedly attached to the tubular body at axially spaced locations therealong; a plurality of temperature activated shape memory wires extending between the rings and electrically connected to and, a power source through the conductors; a power source operatively connected to the conductors, along with an associated control device for selectively heating individual memory wires to a predetermined temperature to cause such wires to contract and thereby effect a bend in the distal end of a catheter as it progresses within the body.

More specifically, the elongated, flexible tubular body is preferably of multi-layer construction including an inner tubular member of relatively stiff plastic material which may enclose fiber optic bundles, air feed channels, electrodes and the like. A flat ribbon-type conductor is spirally wrapped about the inner tubular member and covered with insultaing material.

Fixed attached to an outer surface of the insulating material at axially spaced locations in the distal end area of the tubular member are a plurality of rigid rings, preferably made of aluminum or plastic material. These rings may be fixed to the outer insulating surface by an suitable adhesives, such as known epoxy resins.

Individual titanium-nickel shape memory alloy wires extend between, and are attached to adjacent rings, each pair of rings defining a segment along the length of the catheter-like flexible probe. Each segment preferably has four titanium-nickel alloy wires, spaced 90° apart about the periphery of the probe and extending axially along the probe. The individual wires are electrically connected through the rigid ring to appropriate ones of the conductors beneath the insulating layer of laser welding or other suitable methods including mechanical crimping.

The conductors are connected at the proximal end of the tubular probe to a suitable control device, such as a microprocessor, which is operable to selectively heat various of the tittanium-nickel alloy wires to a predetermined temperature which causes that wire to contract, i.e., shorten its length so as to bend the distal end of the probe in the desired direction.

By sequentially heating selected ones of said wires, it is possible to steer the probe to the desired location within the body.

Further objects and advantages of the invention will become apparent upon consideration of the drawings, detailed description and claims which follow.

BRIEF DESCRIPTION THE THE DRAWINGS

DETAILED DESCRIPTION OF THE DRAWINGS

Figure 1:
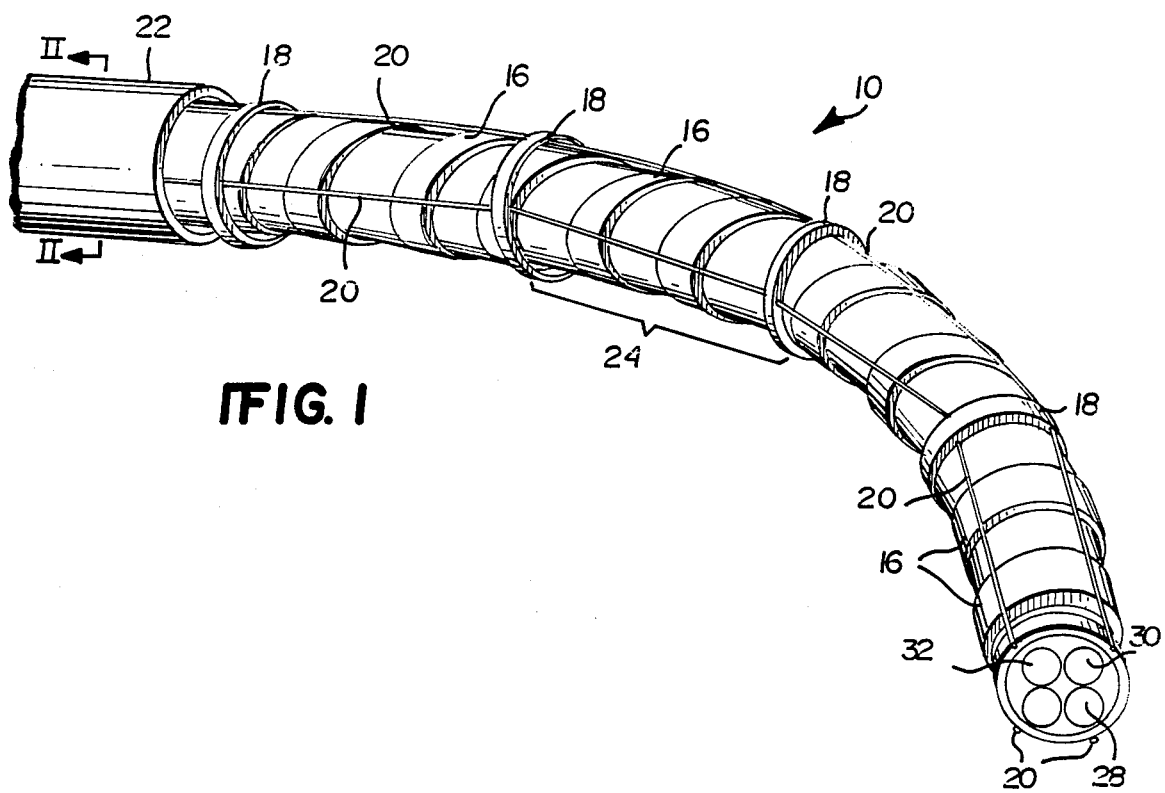
FIG. 1 is a prespective view of a medical probe device in accordance with an exemplary embodiment of the invention, with portions removed to show the internal construction thereof.
Figure 2:
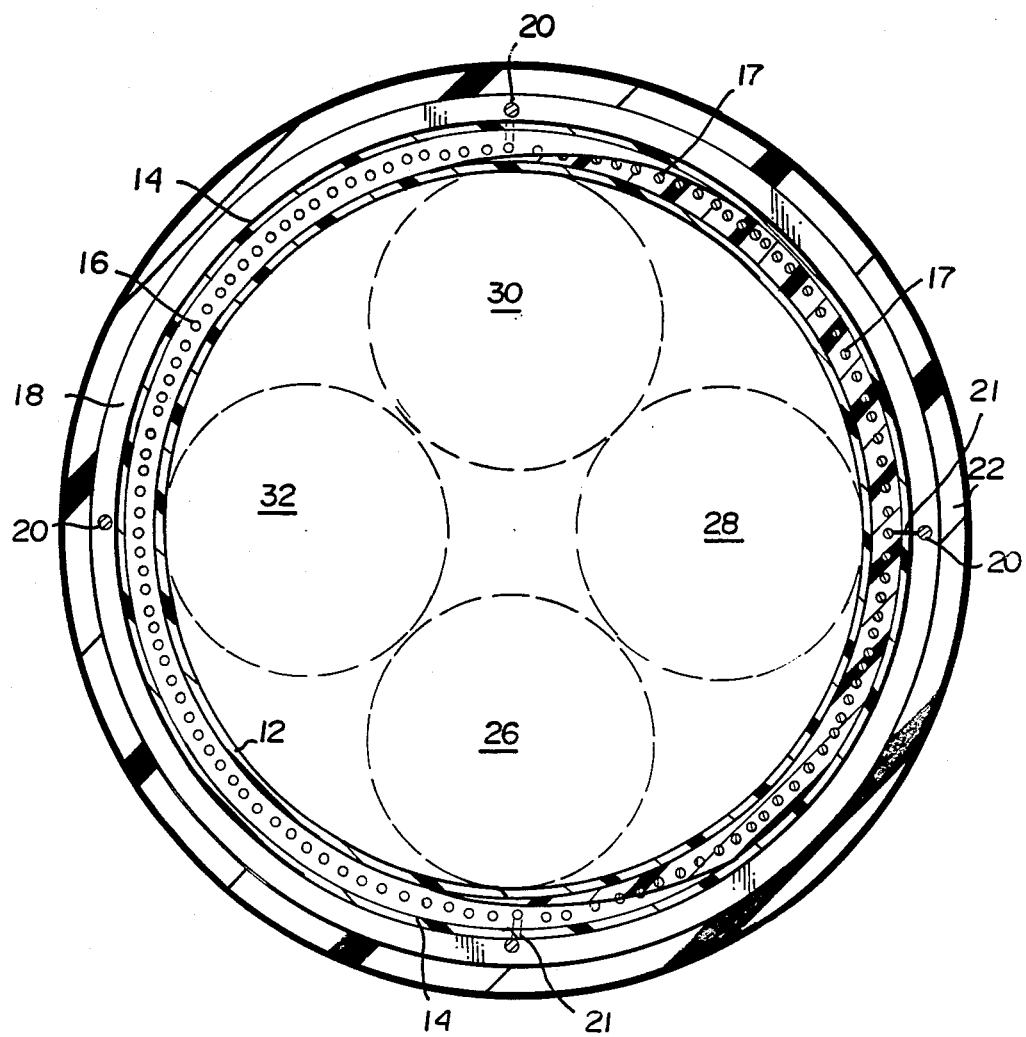
FIG. 2 is a cross-sectional view of the probe device illustrated in FIG. 1, and taken along the line II—II.

Referring now to FIGS. 1 and 2, there is shown the distal end of the catheter, cannulae, endscope or other medical probe device generally referred to by the reference numeral 10. For convenience sake, the probe will hereinafter be referred simply as a catheter, it being understood that the invention applies equally as well to other medical probe devices including those specifically mentioned above as well as others of a similar nature which are designed for insertion within the human or animal body.

The catheter constructed in accordance with this invention is a multi-layered tubular member which includes an inner flexible tube 12 made of a suitable plastic material. Spirally wound about the plastic inner tube 12 is a flat, ribbon-type conductor strip 16 of a conventional type which includes a plurality of electrical conductors 17 arranged in single or multi-layer form. The conductor strip is held in place with respect to the inner flexible tube 12 by a surrounding layer of electrical insulating material 14. It is to be understood that in FIG. 1, the insulating material 14 has been removed to more clearly illustrate the relationship between the conductor strip 16, rigid rings 18 and wires 20, as further described hereinbelow.

Affixed to the outer surface of the insulating layer 14, and axially spaced along the distal end portion of the catheter, are a plurality of rigid, non-conductive rings 18. These rings, preferably made of plastic or aluminum, may be held in place by applying a suitable adhesive such as an epoxy resin to the inner surface of the rigid rings.

Extending between each rigid ring 18 is a set of wires, preferably made from a titanium-nickel shape memory alloy commercially marketed by the Toki Corporation under the name BIOMETAL TM. At least two wires, and preferably a minimum of four wires, extend between each adjacent pair of rigid rings. The four BIOMETAL TM wires are preferably arranged 90° apart about the circumference of the rigid rings. At each end of the individual wires, an electrical connection 21 is made between the wire and an appropriate conductor within the flat, ribbon-type conductor strip by, for example, laser welding, or mechanical crimping. Additional wires may be added to each segment, depending on the degree of steering control desired.

Surrounding this structure is an outer relatively loosely fitting, flexible plastic sheath 22.

Within the multi-layer, tubular construction, there is shown in phantom in FIG. 2, a plurality of tubular members 26, 28, 30 and 32 which may be a fiber optic bundle for illumination and/or viewing purposes, feed lines for air or other fluid, channels for the application of suction, or shape change metal wires used to control miniature surgical tools including cutting and grasping devices.

In the manufacture of the catheter device of this invention, various conventional processes may be utilized to arrive at the construction described hereinabove. For example, where a bundle such as that shown in phantom at 26, 28, 30 and 32 is to be enclosed within the probe, and because of the extremely small size of the probe, e.g., a diameter of from ¼ to ⅜ of an inch, the inner flexible tube portion 12 is preferably formed by dipping the bundle into a heated liquid vinyl composition to form a tubular body surrounding the bundle. After wrapping the flat, ribbon-type conductor strip 16 around the inner flexible tube 12, a similar dipping technique may be employed in order to form the insulating layer 14.

It is also to be understood that rather than a flat ribbon-type conductor, it may be advantageous to form the conductors between layers of insulating material utilizing conventional electroplating and etching techniques.

It is also important in the construction of the flexible, medical probe device of this invention that the inner flexible tube 12 be relatively stiff so as to be able to bend without collapsing, particularly when there is a fiber optic or other bundle within the tube. On the other hand, the outer flexible sheath 22 must be flexible enough to permit some collapse as the individual biometal wires contract to bend the distal end of the catheter.

Figure 3:
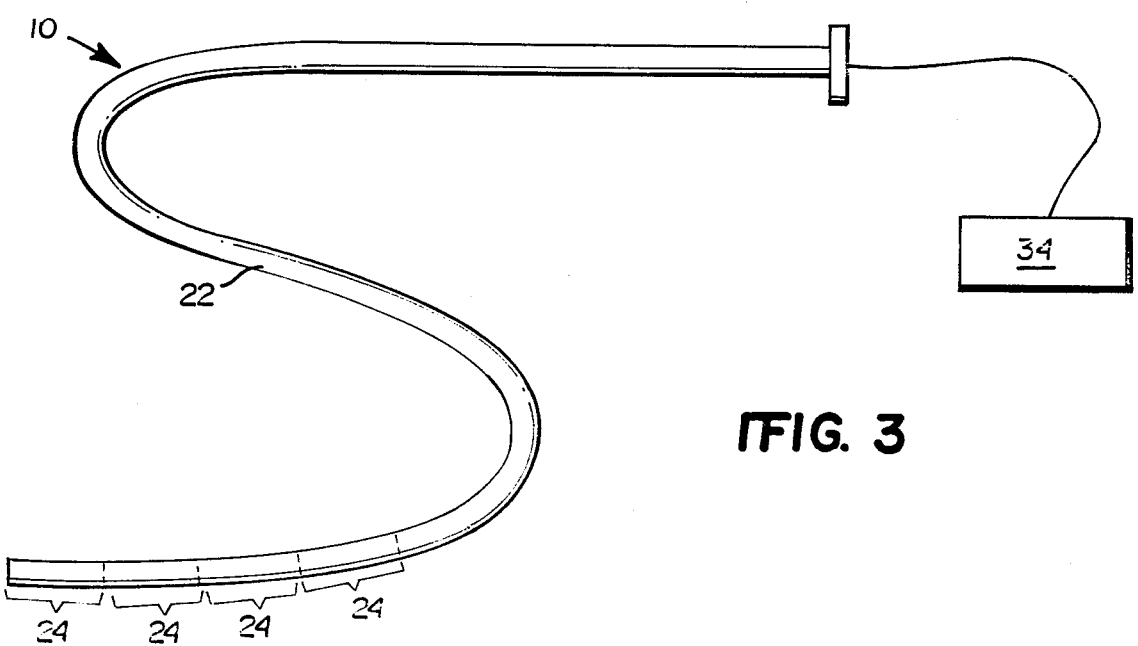
FIG. 3 is a perspective view of the medical probe of this invention connected to a microprocessor control device shown in schematic form.

Referring now to FIG. 3, the catheter device is shown in operative connection to a microprocessor device 34 including a power source, which, as will be appreciated by those skilled in the art, may be programmed to selectively heat individual ones of the biometal wires within a particular segment 24 to cause the distal end of the catheter to bend in the desired direction.

In operation, once the catheter has been inserted in the particular body orifice, incision, artery, vein or other passage, microprocessor 34 is employed to apply very low pulse currents on the order of 3 ohms to selected ones of the biometal wires 20. Low amperage pulse currents are necessary to prevent hot spots from forming and melting the biometal wires. Upon heating to a predetermined temperature, the heated biometal wire will contract and thereby effect a slight bend in the distal end of the catheter. By sequentially heating selected ones of said biometal wires in the various segments, the catheter may be effectively steered in any direction throughout its path of travel in the body. Because selected wires in any or all of the segments may be heated, it is possible to steer the catheter through complex bends in the various body passages.

While the invention has been described in terms of what is presently regarded to be its most practical embodiment, it will be understood by those of ordinary skill in the art that various modifications and changes may be made which will nevertheless remain within the spirit and scope of the invention as defined by the claims which follow.

What is claimed is:

1. A catheter assembly comprising
   an elongated, flexible, tubular body of multi-layered wall construction having a proximal end for connection to a power source, and a distal end for insertion into a body, said tubular body including an inner flexible tube,
   a plurality of pairs of electrical conductors,
   at least one pair of relatively rigid rings encircling said flexible tubular body at axially spaced locations adjacent the distal end thereof,
   a plurality of temperature activated shape memory elements extending between said at least one pair of rigid rings, said elements contractible upon application of heat, each of said elements individually electrically connected to a pair of said conductors and to said power source, and
   control means for selectively heating individual memory elements to predetermined temperatures to effect shape and direction change of said distal end of said catheter within the body.

2. A catheter assembly as defined in claim 1 and further comprising:
an outer flexible sheath concentrically surrounding said flexible tubular body.

3. A catheter assembly as defined in claim 1 wherein said temperature activated shape memory elements comprise metal wires.

4. A catheter assembly as defined in claim 3 wherein said metal wires are composed of a titanium-nickel alloy.

5. A catheter assembly as defined in claim 1 wherein a plurality of pairs of rigid rings encircle said flexible tubular body at spaced locations therealong.

6. A catheter assembly as defined in claim 1 wherein said plurality of sets of conductors are electroplated between insulating layers of said multi-layered wall construction.

7. A catheter assembly as defined in claim 1 wherein said conductors are provided in a flat ribbon-type conductor strip spirally wound within said flexible tubular body.

8. A catheter assembly as defined in claim 1 wherein said control means includes a microprocessor.

9. A catheter assembly as defined in claim 1 wherein at least four temperature activated memory elements extend between each pair of adjacent rigid rings.

10. A catheter assembly as defined in claim 1 wherein said temperature activated shape memory elements are titanium-nickel wires.

11. A catheter assembly as defined in claim 1 wherein said flexible tubular body contains a tube bundle therein.

12. A catheter assembly as defined in claim 11 wherein said tube bundle comprisie a fiber optic tube bundle.

13. A medical probe device comprising an elongated, flexible, tubular member having a proximal end connected to a control device and a distal end for insertion into a human or animal body, said flexible tubular member further comprising means for dividing said distal end into a plurality of axially extending segments, each of said segments comprising a plurality of heat contractable elements comprising titanium-nickel shape memory alloy wires, and said means for dividing said distal end into a plurality of axially extending segments including a plurality of non-conductive, rigid rings encircling to said elongated, flexible tubular member, and for each segment, at least four of said wires are individually attached between a pair of adjacent rings, wherein said heat contractable elements are selectively heated by said control means to effect the shape and direction change of the distal end of the probe device within the body.

14. A medical probe device as recited in claim 13 wherein each of said wires is electrically connected to said control device.

15. A medical probe device as recited in claim 14 wherein said wires are electrically connected to said control device via conductors contained within said elongated tubular member.

16. A medical probe device as recited in claim 15 wherein said control device is operable to selectively heat one or more of said wires to cause said one or more wires to contract and thereby effect a bend in the distal end of said probe device.

17. A medical probe device as recited in claim 13 wherein said elongated, flexible tubular member carries a fiber optic tube bundle.

18. A medical probe device as recited in claim 13 wherein said control device includes means for selectively applying a low pulse current to one or more of said contractable elements to effect a bend in the distal end of said probe device.

* * * * *